(12) United States Patent
Chau (10) Patent No.: US 8,165,345 B2
(45) Date of Patent: Apr. 24, 2012

(54) METHOD, SYSTEM, AND COMPUTER PROGRAM FOR DETECTING AND CHARACTERIZING MOTION

(76) Inventor: Tom Chau, Toronto (CA)

( * ) Notice: Subject to any disclaimer, the term of this patent is extended or adjusted under 35 U.S.C. 154(b) by 945 days.

(21) Appl. No.: 11/952,658

(22) Filed: Dec. 7, 2007

(65) Prior Publication Data

US 2009/0147991 A1   Jun. 11, 2009

(51) Int. Cl.
 *G06K 9/00* (2006.01)
(52) U.S. Cl. .............. 382/103; 348/155; 356/27
(58) Field of Classification Search .......... 382/100, 382/103, 106, 107; 348/14.1, 154, 155; 356/27
 See application file for complete search history.

(56) References Cited

U.S. PATENT DOCUMENTS

| 6,031,568 | A  | * | 2/2000  | Wakitani | 348/169 |
| 6,798,897 | B1 | * | 9/2004  | Rosenberg | 382/107 |
| 6,954,544 | B2 | * | 10/2005 | Jepson et al. | 382/107 |
| 7,113,618 | B2 | * | 9/2006  | Junkins et al. | 382/107 |
| 7,539,327 | B2 | * | 5/2009  | Toyama | 382/103 |
| 7,940,957 | B2 | * | 5/2011  | Ikenoue et al. | 382/103 |

\* cited by examiner

*Primary Examiner* — Anand Bhatnagar (57) ABSTRACT

A method for motion detection/characterization is provided including the steps of (a) capturing a series of time lapsed images of the target, wherein the target moves between at least two of such images; (b) generating a motion distribution in relation to the target across the series of images; and (c) identifying motion of the target based on analysis of the motion distribution. In a further aspect of motion detection/characterization in accordance with the invention, motion is detected/characterized based on calculation of a color distribution for a series of images. A system and computer program for presenting an augmented environment based on the motion detection/characterization is also provided. An interface means based on the motion detection/characterization is also provided.

22 Claims, 4 Drawing Sheets

METHOD, SYSTEM, AND COMPUTER PROGRAM FOR DETECTING AND CHARACTERIZING MOTION

FIELD OF THE INVENTION

The present invention relates to technologies for detecting and/or characterizing motion. The present invention also relates to the field of computer generated virtual or augmented environments. The present invention more particularly relates to augmented environments that allow users to interact with virtual objects and receive feedback.

BACKGROUND OF THE INVENTION

In recent years, there has been considerable interest in the use of computer-mediated environments as assistive technologies for rehabilitation or learning purposes. Much of this interest has revolved around virtual reality or augmented reality systems, a type of computer-mediated environment that generates artificial environments within which the user interacts.

While not necessarily immersive, virtual systems typically plunge the user into a virtual environment where he or she can manipulate virtual objects. Some examples include role-playing virtual environments for adolescents with autism spectrum disorders, virtual reality play interventions and spatial training for children with cerebral palsy, multimodal environments for cognitive rehabilitation, a virtual maze for the assessment of spatial knowledge in teenagers with mobility impairments, and a virtual acoustic space for sensory rehabilitation of children with congenital blindness. These environments have demonstrated potential to improve social participation and enhance specific motor skills in individuals, while maintaining interest and motivation. Part of the appeal as an assistive technology lies in their unprecedented precision in controlling complex stimuli within a test environment, their ability to provide varying levels of environmental interaction, and the early evidence of skill transfer to real world tasks.

Prior art solutions in this field are known, for example, U.S. Pat. No. 5,534,917 for a "Video Based Image Control System", issued to Very Vivid Inc. ('917). '917 discloses building a model of a background that is placed behind a target object, capturing the target object by means of a series of video images that include the background, and detecting motion of the target object analyzing the video images in a digital form, pixel by pixel, by applying threshold values that determine motion.

However, there are limitations to the state of the technology in this area. For example, while most known systems for providing a virtual or an augmented environment use a camera as the primary input device, there is limited ability to filter the input data received to accurately pick up the position, velocity and acceleration of one or more body parts of a user. Furthermore, prior art systems and method for detection/characterization of motion, or for enabling virtual or augmented environments are generally costly, difficult to operate, and/or resource intensive.

In light of the foregoing, a novel computer mediated environment method and system is needed that is relatively inexpensive, easy to operate, and efficient. Particularly in the context of rehabilitation and learning, there is a need for such a method and system.

SUMMARY OF THE INVENTION

In one aspect of the invention, a method for detection and/or characterization of motion of a target is provided comprising the steps of: (a) capturing a series of time lapsed images of the target, wherein the target moves as between at least two of such images; (b) generating a motion distribution in relation to the target across the series of images; and (c) identifying motion of the target based on analysis of the motion distribution.

In another aspect of the invention, a method is provided comprising the further steps of optionally generating a color distribution for the target based on the series of images, and further identifying the motion based on analysis of the color distribution.

In yet another aspect of the present invention, the motion distribution is generated by: (a) defining a region of interest for each of the at least two images that corresponds to the target, or movement of the target; (b) comparing the region for each of the at least two images to establish the difference therebetween; (c) estimating the level of activity associated with the region for each of the at least two images; and (d) based on the level of activity determining whether the level of activity connotes motion, or motion having particular characteristics.

In a still other aspect of the present invention, the color distribution is generated by: (a) defining a region of interest from a plurality of images that correspond to the target, so as to define a first image sample, and a second image sample, each of the first image sample and second image sample including one or more images; (b) calculating the average value of each pixel over the first image sample; and (c) establishing the intensity of each image in the second image sample, subtracting the intensity of each such image from the average pixel value in the first image sample, and creating an image model based on such calculations, the image model defining the color distribution.

In yet a further aspect of the present invention, certain identified motions may be ignored by: (a) obtaining the regions of interest of each of the at least two images to a first plurality of greyscale representations, or converting the regions of interest to the first plurality of greyscale representations; (b) averaging the pixel value of the first plurality of greyscale representations; (c) obtaining a second plurality of greyscale representations of the regions of interest of subsequent images, or converting the regions of interest of subsequent images to the second plurality of greyscale representations; (d) averaging the pixel value of the second plurality of greyscale representations; (e) generating an error value by subtracting the average pixel value of the second plurality of greyscale representations from the average pixel value of the first plurality of greyscale representations; and (f) ignoring detected motion that falls within the error value relative to the previous time lapsed image.

In a still other aspect of the invention, an augmented environment system is provided comprising: (a) a computer; (b) an image capture utility linked to or loaded on the computer; (c) optionally, a display linked to the computer; and (d) a motion detection/characterization utility linked to the computer or loaded on the computer, the motion detection/characterization utility being operable to: (i) capture a series of time lapsed images of the target, wherein the target moves between at least two of such images; (ii) generate a motion distribution in relation to the target across the series of images; and (iii) identify motion of the target based on analysis of the motion distribution.

In yet another aspect of the present invention, a computer program is provided comprising computer instructions which when made available to a computer are operable to define in relation to the computer a motion detection/characterization utility that is operable to: (a) capture a series of time lapsed images of the target, wherein the target moves between at least two of such images; (b) generate a motion distribution in relation to the target across the series of images; and (c) identify motion of the target based on analysis of the motion distribution.

BRIEF DESCRIPTION OF THE DRAWINGS

A detailed description of one or more embodiments is provided herein below by way of example only and with reference to the following drawings, in which.

In the drawings, one or more embodiments of the present invention are illustrated by way of example. It is to be expressly understood that the description and drawings are only for the purpose of illustration and as an aid to understanding, and are not intended as a definition of the limits of the present invention.

DETAILED DESCRIPTION OF THE INVENTION

In one aspect of the present invention, a system, method and computer program is provided for detecting and characterizing motion of a target object. Where motion detection benefits from differentiation between voluntary and involuntary movements of an individual or a real object (collectively referred to as "user"), the system, method and computer program of the present invention involves generation of a movement distribution as particularized below. In a further aspect of the invention, optionally, motion detection/characterization is enhanced by generating a colour distribution as described below, and then correlating the movement distribution with the colour distribution.

It should be understood that motion detection/characterization (or equivalents) refer to the fact that the present invention enables more than just detection of motion, in the sense of detecting its presence or absence, but also enables "characterization" in terms of defining characteristics of motion other than merely its existence. These characteristics may relate to the qualities of the motion, the position of an object generating the motion, the velocity or acceleration of one or more objects generating the motion, the particular area where motion is occurring, or the relative significance of the motion,. This motion characterization aspect of the motion is important in enabling for example the determination of whether or not motion is intentional or not. Further aspects of motion detection/characterization in accordance with the present invention are described below.

Augmented Environment

Motion detection/characterization in accordance with the present invention is described in greater detail below. It should be understood that one of the aspects of the present invention is deployment of the motion detection/characterization technology described herein in connection with a system, method, and computer program for enabling a computer mediated environment, such as for example augmented environments (AE). Unlike virtual environments, augmented environments do not simulate artificial surroundings, but rather augment the real physical environment with additional visual imagery, acoustic response, or other useful information or cues.

Figure 1:
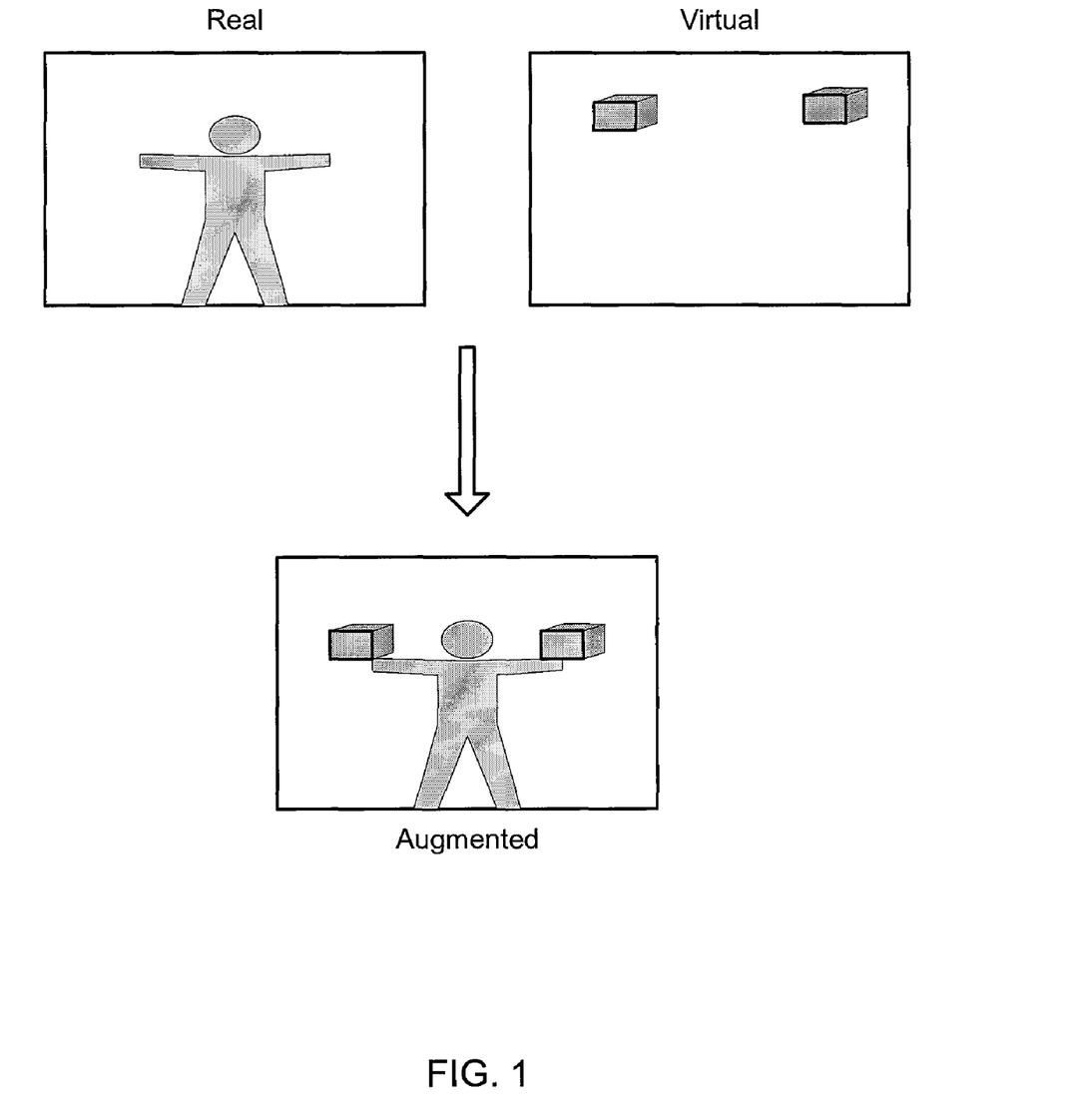
FIG. 1 illustrates an augmented environment combining a real and virtual image space.

These augmentations may be encapsulated in the form of virtual objects within the real environment or as the endowment of additional properties upon real physical objects. FIG. 1 depicts the differentiation among real, virtual and augmented environments. Note that in the augmented environment one may have both real and virtual objects.

Figure 2:
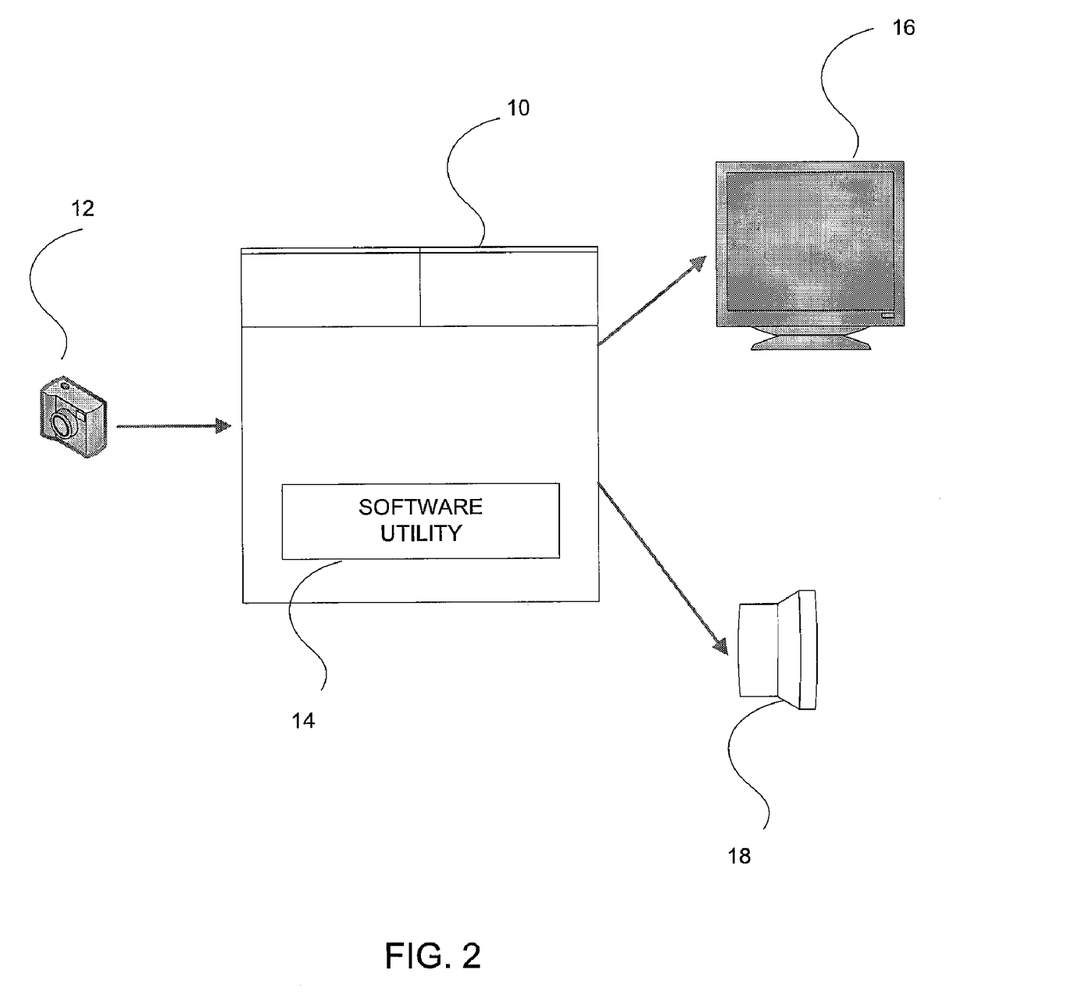
FIG. 2 illustrates a particular embodiment of the augmented environment system of the present invention.

FIG. 2 illustrates a particular implementation of the augmented environment system in accordance with one aspect of the present invention. A computer (10) may receive input about the environment and the user's activities through for example a USB web camera (12) or other suitable image capture means. Loaded or linked to the computer (10) may be a software utility (14) in accordance with the present invention, which may be configured to detect motion as described in this disclosure. Depending on the particular application of the software utility (14), it may also include means for tracking and filtering images.

In accordance with the particular implementation of the present invention, when the user engages in activities that meet certain criteria, such as voluntary motion but also for example intersection with a virtual object, the software utility (14) may be operable to send out appropriate visual and acoustic feedback which may be presented to the user via a visual display (16) and audio speakers (18) linked to the computer (10).

While the present invention is described primarily in relation to a computer mediated environment which is an augmented environment, it should be understood that the system, method, and computer program described may also be adapted to enable a virtual environment.

Motion Detection and Characterization

Figure 3:
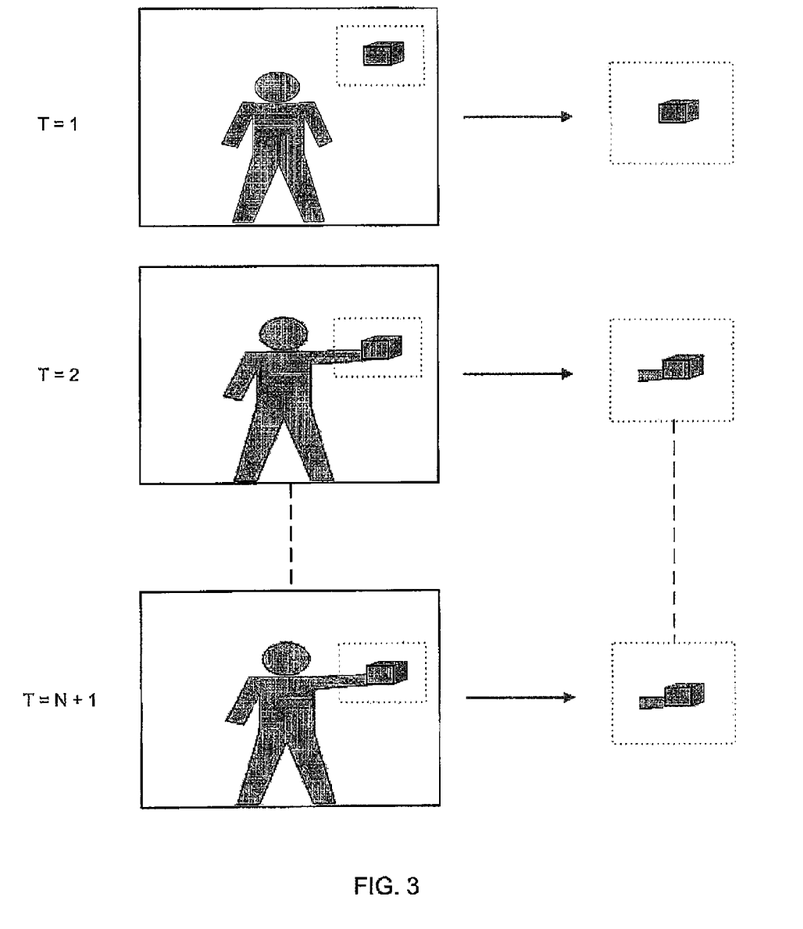
FIG. 3 illustrates the method of motion detection and/or characterisation provided by the present invention.

FIG. 3 illustrates the method for motion detection/characterization provided by the present invention, in one aspect thereof. Each time a new image frame is captured by the image capture means, in accordance with one aspect of the present invention, there may be an analysis whether the image frame indicates significant activity on the part of the user relative to neighbouring (in the time domain) image frames. The capture of image frames is described below in the section entitled "Image Stream Capture", which constitutes an example of image capture for enabling motion detection/characterization in accordance with the invention.

The analysis may be performed on each virtual object separately. Specifically the set of images may be scanned for each virtual object to see if there is any significant activity on the part of the user. The following steps may be repeated for each virtual image.

1. Extract the region of the image corresponding to the virtual object in question.

Prior art methods are known for extracting or isolating specific regions of digital images. The size of the portion of the image to be extracted may be chosen based on the distance between neighbouring virtual objects, or other criteria. It may be preferable in certain implementations to ensure the maximum size of the portion of the image to be extracted such that the portion may contain at most one virtual object.

2. Find the difference between corresponding regions of successive images.

The procedure may be expressed as follows:

$$CurrentImageDifference = \sum_{ij} |CurrentImageRegion_{ij} - LastImageRegion_{ij}|$$

CurrentImageRegion and LastImageRegion may be modelled as 4-D matrices, where the four dimensions consist of red, green and blue (RGB) matrices of a certain width and height. The CurrentImageDifference is therefore also a 4-D matrix of RGB values, with each submatrix denoted as $CurrentImageDifference_R$, $CurrentImageDifference_G$, and $CurrentImageDifference_B$ for red, green and blue matrices respectively.

3. Estimate the current level of activity.
   This may be expressed as follows:

$$Activity = \frac{1}{MaxActivity}\begin{pmatrix} CurrentImageDifference_R + \\ CurrentImageDifference_G + \\ CurrentImageDifference_B \end{pmatrix}$$

where the maximum activity is given by:

MaxActivity=Test Region Width×Test Region Height×255×3

4. Determine the threshold activity.
   The threshold activity may be determined based on a tuneable sensitivity level. The adjustment of the sensitivity level may allow for the detection of different degrees of movement from very minute (e.g. a moving finger of an individual) to gross movements (e.g. the individual waving her arms). In this way, the system may be operable to accommodate any magnitude of movement. The range of movement may only be limited by the camera's resolution. This is particularly useful for users who are not able to produce typical gross excursions of their limbs or objects that do not move significant distances. Sensitivity may be increased significantly to accommodate minute movements or may be appropriately decreased to accommodate users and real objects that may be expected to move significant distances.
   If sensitivity of the virtual object has been specified to be the lowest possible (i.e. no sensitivity to movement) then the threshold may be set to a very large value. The threshold value may range, for example from zero to ten where zero is the most sensitive threshold and ten serves as an unreachable threshold such that movement cannot be detected. In one embodiment of the computer program of the present invention, the threshold may be set using a threshold control means, for example via a standard slider graphical user interface.
   If the user sets sensitivity to 0, the threshold value may be 1. If the user sets sensitivity to a non-zero value, the following formula may be used to determine the threshold:

$$Threshold = \frac{1}{2}\left[1 - \tanh\left(\frac{Sensitivity}{100} \times 6 - 3\right)\right]$$

Using the above formula, the sensitivity may range from 0 (least sensitive) to 100 (most sensitive).

5. Compare the current activity against the activity threshold described above.

Optionally, in another aspect of motion detection/characterization in accordance with the present invention may be the use of dwell times (i.e. capture and analysis of the amount of time during which the user moves into the region of a particular virtual object). Adjusting dwell time requirements properly may prevent the virtual objects from being activated when the user accidentally moves into a virtual object's region of interest. In other words, this may allow the user to make movements without worry of accidentally activating nearby virtual objects.

The use of dwell times relies partially on the proposition that if the activation is intentional, then the user may move in the region of the object for a time which exceeds the dwell time. Similarly, for turning off the object, the user may be required to exit the object's region of interest for a certain period of time.

When the user continues to move within the object's region of interest, the activation may be sustained, much akin to holding down a piano key.

After the above step of checking whether the activity level is greater than the current threshold, the second step may be to check if the dwell time on the virtual object spatial area has been exceeded. If the dwell time has not yet been exceeded, the current time may be recorded as the start of activity, and the activity levels continue to be monitored in subsequent image frames. In the computer program of the present invention, the dwell time may be set by means of a dwell time control utility, which is accessible for example via a standard slider graphic user interface presented by the computer program of the present invention.

If the dwell time on the virtual object spatial area has been exceeded, the motion detection/characterization system may record an activation of the virtual object. Furthermore, the motion detection/characterization system may optionally record the duration of activation.

A similar process may be used to determine when the object is no longer active. If the activity level is less than the threshold, the system may check if the object is currently active. If it is, the system may check if the "OFF" dwell time has been exceeded. If not, the system may note the current time as the beginning of activity cessation, and continue to monitor activity. If the "OFF" dwell time has been exceeded, the system records a deactivation of the virtual object.

The method for motion detection/characterization described above may be implemented by means of an algorithm in a manner that is known, and implemented to a computer program in a manner that is also known so as to present a motion detection/characterization utility. In one aspect of the computer program of the present invention, a motion detection/characterization utility is provided that may be loaded on a computer, or otherwise made available to a computer, in order to enable the functions described. These functions may also be integrated with other applications by providing programming implementing these functions to such other applications.

In a particular aspect of the present invention, the motion detection/characterization utility may include means for controlling the threshold or dwell times as described above.

It should be understood that motion detection/characterization in accordance with the present invention may give users greater convenience and minimize inadvertent activations of virtual objects. Minimization of inadvertent activations may prevent virtual objects being activated due to non-targeted body parts, camera movement, and/or ambient lighting changes.

The present invention also contemplates a number of related methods that enhance motion/detection characterization as described. These methods may be implanted as filters or image processing utilities that are included or linked to the motion detection/characterization utility described.

Image Stream Capture

Figure 4:
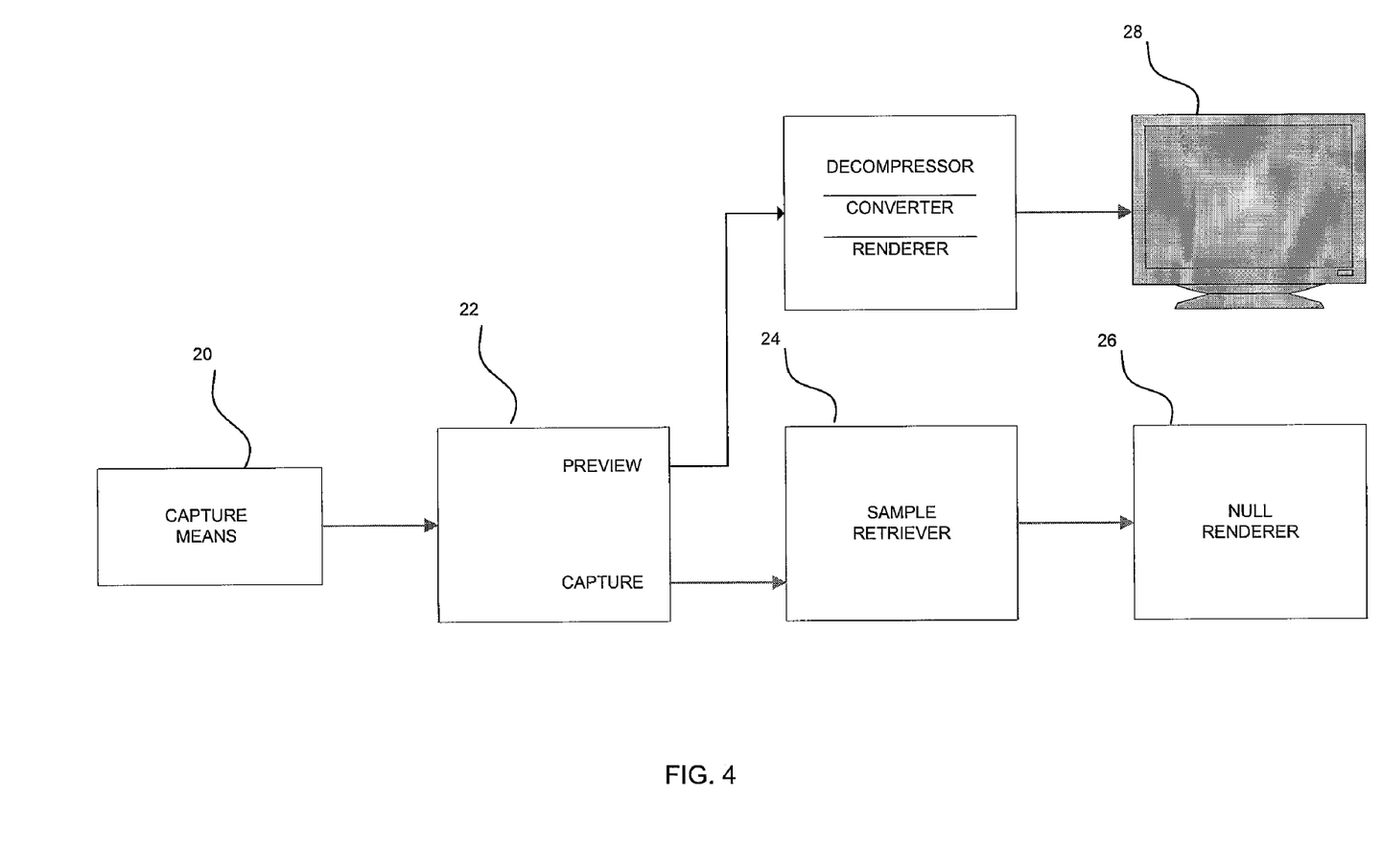
FIG. 4 illustrates a particular example of filters operable to optimize performance of the present invention.

FIG. 4 illustrates the image stream system and method, in one aspect of the invention. The system may use a media-streaming architecture (MSA) such as DirectShow™ for image data acquisition. The MSA may first receive the image data from an image capture means (such as a USB camera) (20), and then may put the stream of data through a filter graph. On the filter graph, the image capture means may appear as a video input source filter which may automatically be connected to a filter (22) operable to split the input data into preview and capture outputs, such as a Smart Tee™ filter. The preview stream may render the video onto the capture screen (28), and the capture stream may be used for data retrieval.

The motion detection/characterization technology of the present invention may only require use of the capture stream. The capture output for example may be connected to a filter operable to retrieve samples (24) as they pass through the filter graph, such as a Sample Grabber™ filter. The sampling frequency may be set, for example at 10 Hz (10 samples retrieved per second). The sample retriever (24) may further be connected to a filter operable to discard retrieved samples (26), such as a Null Renderer™. This may only be required if the sample retriever (24) used requires a downstream connection.

Grey-Scale Baseline Model

The present invention may optionally use a novel grey-scale baseline model. The grey-scale baseline model in relation to the invention operates as a filter which screens out intended activations from those due to noise, such as the flickering of a display screen captured by a camera. For the sake of convenience, hereinafter the intended activations will be referred to as "candidate activations," and the activations as a result of noise as "noise activations."

Image Data Retrieval and Grey-scale Conversion

Once the user creates a virtual object on a capture screen (28), motion detection/characterization may commence. The motion detection/characterization method of the present invention may be specific to each virtual object, which means the following events may occur with the creation of every virtual object. The sample retriever (24) may begin to acquire image samples, which may be subsequently retrieved for analysis. Each time a sample is retrieved, the data from the region of interest (ROI) corresponding to the location of the virtual object on the capture screen may be extracted and copied into a buffer. The image data may be then converted to grey-scale values via for example a function which employs a formula, one operable example being $Y=0.299*R+0.587*G+0.114*B$, with Y representing the luminance value.

Grey-scale Baseline

For a set number of the first samples, such as five (i.e. the first 0.5 second after the virtual object is created if the sampling rate is 10 Hz), it may be assumed that there has yet to be any attempt of activation by the user. Therefore, the data samples may solely contain the values of the background. The grey-scale pixel values of the ROI from these first five samples may be collected and stored in a memory. When the fifth sample is collected, the average value of each pixel in the ROI over these five samples may be computed. The average values may be subsequently stored into a separate buffer. Thus, there may exist a buffer which contains the average background luminance values of each pixel in the ROI. This buffer may be referred to as the "grey-scale baseline."

Grey-scale Model

For a next set of images, for example the next five images (i.e. up to one second after the virtual object is first constructed), the same assumption as before may be made: the user has yet to attempt to activate the virtual object. Consequently, the data samples from these next five samples may also contain only the values of the background. The luminance values of each of the next five samples may be stored in five separate buffers. A comparison operation may then be made between each of these five buffers and the grey-scale baseline; the pixel values in each of the five buffers may be subtracted from the corresponding pixel values in the grey-scale baseline. The results of this comparison operation may then be stored in a buffer, from which a statistical distribution is created. This statistical distribution may represent the distribution of the natural luminance fluctuations in the ROI. These luminance differences may be due to the natural flickering and the natural inconsistencies of the camera or other hardware. This statistical distribution may be referred to as the "grey-scale model." The grey-scale model may resemble a normal distribution. As a result, subsequent parts of the motion detection/characterization algorithm may assume that the grey-scale model is Gaussian.

Critical Values of the Grey-scale Model

From the grey-scale model, the mean and standard deviation may be calculated. The value of the mean may be very small and close to 0 since the natural luminance differences in the pixels may be expected to be minimal. Critical Z-score values corresponding to a 5% significance level may then be selected. The default values for a unit standard normal may be ±1.96 (this Z-score value may be varied to represent different sensitivity levels, as described below in this section). Using the values of the mean, standard deviation, and a Z-score (for example of ±1.96) the algorithm may then calculate the two corresponding critical values for the grey-scale model at hand, $$X_{critical}=[Z_{critical}*(\text{standard deviation})]+\text{mean},$$

where $Z_{critical}$ denotes a critical value of a standard normal distribution.

These two critical values may serve as the boundary values which may be used later to distinguish candidate activations from noise activations.

Testing for Motion (Deviation From the Grey-scale Model)

From each further sample (for example, the eleventh sample on), each image sample retrieved from the sample retriever (24) may be compared to the grey-scale baseline. The results of this comparison may be stored in a buffer, from which a mean may be calculated. This mean may represent the average difference in the luminance of all the pixels in the ROI from the pixels in the grey scale baseline. This mean may be referred to as "the average change." In other words, for each subsequent image sample, the average change (averaged over all pixels in the ROI) may be computed from the grey-scale baseline. This average change may then be tested against the grey-scale model. Should the average change fall within the previously calculated boundary values, the program may interpret it as a noise activation (i.e. natural fluctuation) and ignore it. However, should the average change fall outside of the critical values, the program may label it as a candidate activation. Thus changes in the luminance of the pixels from natural events such as flickering may be minimal and, therefore, the average change may always fall within the critical values of the grey-scale model.

However, in the event of intentional activations by an object, a much larger difference in the luminance of the pixels in the ROI may result. Therefore, the average changes from these events may fall outside the boundary values, thus providing a mechanism to distinguish noise activations from candidate activations.

After a sample manages to "satisfy" the grey-scale model and may be labelled a potential activation, the technology of the present invention may proceed on to the RGB models, which may check to see if the sample contains the data values that correspond to the colour of the targeted body part. This process is described below in the section entitled "The RGB Models".

The computer program of the present invention, for example, may allow the user to set the value of the Z-score which is used in the calculation of the boundary values. The user may choose a value within a set range, for example between 1.00 and 3.00. By choosing a greater value for the Z-score, it may mean that the interval within which all motion will be regarded as natural activation may be larger, thus rendering the virtual object less sensitive (since a greater absolute value for the average change may be required for it to be labelled as a potential activation). Conversely, a smaller value for the Z-score may translate into a smaller interval, making the virtual object more sensitive. In this manner, the user may set the sensitivity of motion detection/characterization for the virtual object as required.

The construction of the grey-scale model by operation of the invention may repeat if for example the computer program of the present invention detects global motion from inadvertent camera movement. This aspect of the present invention is further described below. This may allow the grey-scale baseline and the grey-scale model to be updated with the new background due to the different camera positioning.

Dwell Time

Optionally, the motion detection/characterization utility of the present invention includes a dwell time feature (which may be implemented for example as a routine) that may prevent inadvertent activations by non-target body parts. The dwell time may be used so that the system detects sustained motion within the virtual object for a specified period of time before deeming the activation as valid.

The dwell time may be implemented using the grey-scale model and a counter variable, for example. For example, where an applicable algorithm (provided in a manner that is known) takes in samples at a rate of 10 samples per second (i.e. 10 Hertz), each time a sample is retrieved a "success counter variable" may be modified according to whether or not the sample satisfies the grey-scale model. If the sample satisfies the grey-scale model, it may increment the success counter variable. Otherwise, the success counter variable may be reset to 0. In this way, the success counter variable may track the number of consecutive samples which manage to satisfy the grey-scale model. The algorithm may interpret an activation attempt to be legitimate if the success counter variable reaches a value of 10 (where the dwell time is set to 1 second). In other words there must be 10 consecutive samples satisfying the grey-scale model before the attempt to activate may be considered valid. If any one of the consecutive images fails to satisfy the grey-scale model before the success counter variable reaches 10, the success counter variable may be reset to 0, thus restarting the count again. The success counter variable may also reset to 0 after it reaches a value of 10, so that it may be reused again after a valid activation attempt.

In the computer program aspect of the present invention this period of time (dwell time) may be varied by the user. A typical selection may be 1 second. In other words, motion has to be detected continuously in the virtual object for at least 1 second before the program considers it to be a legitimate attempt to activate the object. This may then filter out accidental activation attempts by non-targeted body parts, because such inadvertent activations may not usually be sustained consistently longer than 1 second. The user may alternatively be given the option to set the number of consecutive images that must satisfy the grey-scale model before an activation attempt is considered valid. By modifying this number, the user may thus set the dwell time of each virtual object.

The RGB Models

Optionally, the motion detection/characterization utility of the present invention is operable to generate RGB models and apply the RGB models as colour filters for the targeted body parts. Upon initial activation of each virtual object, an applicable algorithm (provided in a manner that is known) may collect a few seconds of data and determine a colour range for the admissible pixel colours. These colour ranges may be the RGB models. Subsequent movements may then activate the virtual objects only if their average values fall within these colour ranges.

Creating the RGB Average Buffer Upon Object Activation

The RGB models may initially be generated using data collected during the initial activation of the virtual object. By doing so, an assumption may be made that the initial activation is an intended activation by the targeted body part. For this reason, the algorithm may be set up so that the initial activation of a virtual object has a longer than normal dwell time. For example the initial activation dwell time may be set to 150% of the normal dwell time. This increased dwell time may allow more samples to be collected, thus making the data more consistent and reliable. As a consequence of the dwell time mechanism, the initial activation of a virtual object may be interpreted by the program to be for example the first 15 consecutive images (where the normal dwell time requires 10 consecutive images) which manage to satisfy the grey-scale model.

Upon initial activation, the data values from the initial images may be stored in separate buffers. It should be noted that, in a representative example embodiment, these 15 samples may be the original RGB-values of the ROI and not the grey-scale-converted values. When each sample undergoes the grey-scale conversion, a copy of its original RGB-values may be made so that if the sample does manage to satisfy the grey-scale model, the copy of its original RGB-values may be used for analysis in the RGB models. With the data from the samples stored in separate buffers, the program may proceed to calculate the average value of each colour channel of each pixel in the ROI over the samples. These average values may then be stored in a separate buffer, which may be referred to as the "average RGB buffer."

Selecting Pixels for RGB Model Construction

A copy of the average RGB buffer may be made, and this copy may be converted into grey-scale values. This buffer of grey-scale values may then be compared to the grey-scale baseline (which may contain the average luminance value of each pixel of the background in the ROI). Pixels with luminance differences greater than a predetermined threshold (for example, ±10) may be noted, and the RGB values of the corresponding pixels may be extracted from the average RGB buffer. By doing so, all the background pixels (non-moving pixels) may be filtered out, and only the pixels of the targeted body part may be retained for building the RGB models. The extracted data may be split into 3 separate colour channels:

red, green, and blue. At this stage, there may be three separate buffers (for red, green, and blue), and each may contain the average colour intensity of every pixel of the targeted body part.

Estimating Critical Values for the RGB Models

The three colour buffers may be sorted to arrange the data in each in ascending order. The sort may be accomplished by a number of sorting means, for example a selection sort known as heapsort. Preferably, a heapsort may be run to conserve stack memory in a computer system.

After the data values in the 3 colour channel buffers are arranged in ascending order, boundary values may be calculated from each of the buffers. For example, the lower boundary value may be set at the $10^{th}$ percentile of the data, and the upper boundary value may be set at the $90^{th}$ percentile. These 3 colour ranges ($10^{th}$ to $90^{th}$ percentiles) may be the RGB models, and all subsequent potential activations may be subjected to comparison to these RGB models.

Color Specific Activation

After the initial activation, the dwell time may be reset to the normal dwell time. Subsequent attempts to activate the virtual object may first go through the grey-scale model comparison. If the attempt is labelled as a candidate activation, the required consecutive samples (for example, 10) may undergo testing with the RGB models. As with the construction of the RGB models, these consecutive samples may first be averaged out and screened, so that only the pixels of interest (pixels from the targeted body part) may be collected for analysis. The screening procedures may be done in a similar fashion as before; the average values may be converted to grey-scale values, and a luminance comparison may be made with the grey-scale baseline. The pixels whose luminance difference is greater than ±10 may then be noted and extracted from the corresponding average RGB buffer. The extracted data may be split into its 3 colour channels: red, green, and blue. The program may then calculate a mean from each of the 3 colour buffers, and each mean may be compared with the corresponding RGB models. If the mean falls within the range of the colour model, it may have satisfied the model. Otherwise, it may have failed the model. The candidate activation may be deemed a successful activation only when all the three models (R,G and B) have been satisfied. If the potential activation fails any of the three colour models, it may be labelled as an unsuccessful activation.

Dynamic Updating of RGB Models

In order to account for changes in lighting and perhaps in skin colour of the targeted object or user's body part, the entire procedure of creating the RGB models may repeat itself at predetermined intervals, for example every 1200 samples. At a sampling rate of 10 Hz, this translates into every 2 minutes. Recreating the RGB models may permit the RGB models to be updated allowing the user to still activate the virtual object in the event of ambient lighting changes or skin colour changes.

Level of Activation

A level of activation of a virtual object may be determined. Once an activation attempt has been labelled as a successful activation, the program may refer to the average RGB buffer and count the number of pixels that have been extracted (recall a pixel will be extracted if its luminance has a difference greater than, for example, ±10 when compared to the grey-scale baseline.). The number of extracted pixels therefore may correspond to the number of pixels representing the targeted body part. This number may then be expressed for example as a percentage of the total number of pixels in the ROI (the number may be divided by the total number of pixels in the ROI and then multiplied by 100). This percentage may then be used as the level indicator, with 0 being a minimum level and 100 being a maximum level. Depending on the implementation of the present invention, the level of activation may communicate an intensity to a user.

Sustained Activation

Sustained activation may come into play when the user leaves his or her targeted body part within the virtual object. If the user does not move his or her body part, the system and computer program of the invention may interpret it as no motion. However, if the user constantly moves his or her targeted body part within the virtual object, the program may interpret it as sustained motion.

Sustained activation may be only triggered after an attempt to activate has been labelled a successful activation. After an activation attempt has been deemed successful, a copy of the grey-scale version of the average RGB buffer (recall that this buffer stores the average values of the RGB values of the pixels of the targeted body part) may be made, and the dwell time may be set to 1 sample (which is the amount required to satisfy the grey-scale model before it is labelled a valid activation attempt). The reason for shortening the dwell time may be for the purposes of checking whether or not the targeted body part remains in the virtual object. Too long of a dwell time will be impractical, since the user may be unlikely to leave his or her targeted body part within the virtual object for more than a few seconds. If the next sample is able to satisfy the grey-scale model, its data may be taken in and screened for the pixels of interest. The data may then be checked to see if they satisfy the RGB models, and if they do, the RGB values from the sample may be converted into grey-scale values. A copy of the buffer containing the grey-scale values may then be made.

At this point, there may be in the memory two buffers containing the grey-scale values of the pixels of interest. This process may repeat for another several (for example, the next two) consecutive images, and if they manage to satisfy all the models, a copy of the grey-scale values may be made. There may now be a plurality of (for example, four) buffers stored in the memory, each containing the luminance values of every pixel of the targeted body part (the first buffer may be averaged over 10 samples due to the 1 second default dwell time, and the remaining three buffers not averaged at all, since the dwell time is set at 0.1 second). These four buffers may be referred to as Buffer 1, Buffer 2, Buffer 3, and Buffer 4 respectively.

After making a copy of Buffer 4, the system and computer program of the present invention may perform a comparison operation between Buffer 1 and Buffer 2, Buffer 2 and Buffer 3, and Buffer 3 and Buffer 4. This comparison operation may check for the number of pixels whose luminance difference is greater than a predetermined threshold (for example, ±5). By counting the number of pixels whose luminance difference is greater than the threshold, a quantitative indication of the level of motion between the data in the consecutive buffers may be obtained. The comparison operation may yield three numbers, one for the level of motion between Buffer 1 and 2, the second for Buffer 2 and 3, and the last for Buffer 3 and 4.

These three numbers may then be averaged out and expressed as a percentage (the averaged value is divided by the total number of pixels of the targeted body part and then multiplied by 100). This final percentage value may represent the average level of motion between the data in Buffer 1, 2, 3, and 4. If this value is above a predetermined threshold value, the computer program of the present invention may interpret it as sustained motion within the virtual object. However, if the average level of motion is below the threshold value, the computer program may view it as no motion.

In the above description, it should be noted that if any of the 3 subsequent samples (in our case above, the 3 samples in Buffer 2, 3, and 4) does not satisfy the grey-scale model or the RGB models, the program may immediately loop out of the sustained-activation algorithm and interpret it as no motion.

The sustained activation may continue as long as the user keeps on moving his or her targeted body part within the virtual object spatial area. The description above details the algorithmic procedures, to calculate the level of activity for the first round of sustained activation. Should the sustained activation continue for subsequent rounds, a shifting-window method may be employed to calculate the level of activation between the consecutive samples.

Programmatically, this means that instead of waiting for four buffers to be collected and then doing the comparison operation to extract the three values, the program may take in the next sample and immediately do the comparison operation with both the old and new samples. Using the same name convention in the above description, it means that after the fifth sample is taken in and occupies Buffer 5, the program may do the comparison operation between Buffer 2 and 3, Buffer 3 and Buffer 4, and Buffer 4 and Buffer 5. The three values may then be averaged out and expressed as a percentage, indicating the average level of motion between the consecutive samples. This process may repeat continuously yielding a value every interval (for example, every 0.1 second), until the user stops moving his or her targeted body part, or until the user removes his or her targeted body part from the virtual object. The method of shifting-window may be used to minimize the delay in calculating the average level of motion. If the program has to wait until four samples are collected before it can proceed to calculate the average level of motion, there may be a delay (of for example 0.4 seconds if the dwell time for each sample is 0.1 second). By using the shifting-window method, this delay may be reduced to the single sample dwell time for subsequent rounds of sustained activation beyond the initial round.

Global Motion (Camera Movement)

Another aspect of the present invention is "global motion detection/characterization". Occasionally, the image capture means (for example, a camera) may be accidentally moved (or knocked over), which may normally mislead the program to interpret simultaneous attempts to activate all the virtual objects. In order to avoid this, a detection mechanism is implemented to check for global motion due to camera movement. The computer program of the present invention may constantly monitor two lines of pixels from the capture image: the top line and the bottom line. If the program detects a significant change in the luminance value in a majority of these pixels, it may view it as global motion. Once global motion is detected, the program may enter an infinite loop, only exiting when the global motion stops. Upon exiting the loop, the general algorithm implemented to the computer program may restart and all the grey-scale models and RGB models may be rebuilt with the new and updated data. In this manner, the user may be saved some time and convenience.

The method for implementing global motion detection/characterization may be similar to the procedures for calculating the level of activation. The difference may lie in that the pixels of interest may be the top line and bottom line of pixels of the capture screen. At each interval of a predetermined number of samples (for example, 5 samples equivalent to 0.5 second if the sampling rate is 10 Hz), a comparison operation may be performed on the two lines of pixels. The comparison operation may compare the luminance values between every fifth sample, noting the number of pixels whose luminance difference is greater than a predetermined threshold (such as ±5). The result may be expressed as a percentage. If this percentage value exceeds a set threshold (for example, 90% for both the top line and the bottom line of pixels) the program may interpret it as global motion. Otherwise, the program may ignore the motion and resumes to normal operation.

Once global motion is detected, the computer program may initiate an infinite loop. While in this infinite loop, the computer program may continue to monitor the two lines of pixels, doing the same comparison operation as described before. If the percentage values still exceed 90% for both the top line and bottom line, the loop may repeat itself. The computer program may exit this infinite loop when at least one of the percentage value is below 90%. After the computer program exits this loop, it may enter a sleep mode for a predetermined time (for example 3 seconds) after which the computer program may start again. The delay may allow the user to settle down the image capture means before data acquisition restarts. When the computer program restarts, it may go through the procedures for building the grey-scale model and RGB models again (as described before), as if this is the first time the computer program has started. By doing so, the grey-scale baseline and the grey-scale model may be automatically updated with the new background data, thus allowing the user to resume normal operation without having to go through any manual calibration settings. This functionality, therefore, may add to the user's convenience.

Implementation

The motion detection/characterization functionality described above can be implemented to as or to a number of different systems or computer programs, in a number of different areas. A few examples of such implementations are provided below.

Movement-to-Music

In a particular implementation of the system, a Movement-to-Music (MTM) system may be provided by implementing the motion detection/characterization technology described thereby providing an affordable musical play system. The MTM may be best understood as a modification of the representative system described earlier, and may incorporate automatic movement recognition technology that is non-contact and non-invasive. Usability of such a system has been demonstrated based on studies conducted with children.

In accordance with one aspect of the MTM system, the system may capture the image of a child through a small, economical web camera linked to the computer. Implementation of the computer program of the present invention as a custom computer software program may allow the camera to detect a wide range of movement, from very small ones, such as raising the eyebrows, to very large ones, such as waving an arm. The child may see a reflection of him or herself on a television screen or computer monitor, which may be connected to the computer. Superimposed on the child's reflection may be a number of coloured shapes. These coloured shapes may be virtual in that they exist only in the computer environment. However, each shape may correspond to a region of physical space around the child. When the child's moves a part of his or her body into the space occupied by a virtual shape, a musical tone may be triggered. This auditory feedback combined with visible changes in the shape's transparency may indicate to the child that the shape has been successfully activated. The number of shapes and their location, colour, size and response properties may each be configurable.

The MTM system may provide a training product that surpasses the prior art as currently there are no simple training products available that enable an individual with special needs or an individual learning to express themselves fully in a creative manner. The MTM system may represent a significant leap in this direction.

In a particular embodiment of the MTM system, a Virtual Musical Instrument (VMI) that implements the described motion detection/characterization techniques may be provided. By moving one's hands into different areas of space, the individual may be able to play different notes, chords, instruments and musical passages. This novel software has numerous applications including in physical therapy, the virtual world of music, and the world of entertainment.

According to a particular aspect, the present invention may allow children with poor motor control such as in cerebral palsy (CP) or those with hypotonia such as in spinal muscular atrophy (SMA) type 2, to make music via bodily movements, both as a structured educational activity and an unstructured play activity.

An AE system for paediatric rehabilitation may consist of the components outlined above. In this particular realization, the child may see an image of him or herself on the visual display, superimposed with coloured circles representing different musical notes.

Circles may be the virtual objects or augmentations within the real environment. When the child interacts with one of these virtual notes, through movement of fingers, hands, arms, head or body, the note may become transparent on the visual display and the appropriate tone may be sounded in the likeness of a selected music instrument. The technology may be non-contact in that the child need not need touch any physical devices, but may simply move through the surrounding space.

The virtual objects, i.e. notes, may be completely configured by a therapist or parent for each individual child and piece of music. The colour, volume, timbre, tone, spatial position, size and multiplicity of the virtual notes may be adjustable by operation of the computer program product of the invention. Additionally, the sensitivity of each note to movement and on and off dwell times may be individually adjusted. These dwell and sensitivity variables may allow the technology to filter out sporadic involuntary movements, and accommodate both fast and slow movements simultaneously.

The configurable position and size of the activation regions may facilitate successful activation regardless of one's range-of-motion or location of bodily control site. For each virtual note, the volume of the auditory feedback may increase as more of the spatial area corresponding to a note is activated. Notes may be held for different temporal values by sustained movement within the region of activation. Hence, this augmented environment not only may provide access to musical tones, but may also offer control of volume and timing of the feedback, much akin to a conventional instrument.

Where activated, a sound proportional to the magnitude of average activity over the last N frames where the threshold has been exceeded may be outputted. This may be expressed as:

$$AverageActivity = \frac{\sum_{last\ N\ frames} Activity}{N+1}$$

To determine the appropriate output volume, a decay factor may be used. This may be expressed as:

$$\delta = 4.6052 \times \frac{(AverageActivity - \text{Threshold})}{\text{Threshold}}$$
$$\text{Volume} = 0.5 \times VolumeSetting \times (1 - e^{-2\delta})$$

In the computer program of the present invention, the VolumeSetting variable may be set by a control, such as a slider.

Volume may be controlled also by motion by determining the magnitude of activation. If the user produces greater movement, the virtual object may generate a louder sound. Likewise, less activity (but still above threshold), may produce a softer sound.

Deactivation of the virtual object may turn off the sound of the current virtual object.

Volume may also be determined by level of activation, as described above. Furthermore, a sustained activation may result in a continuous sound.

Similar to the VMI, the user may interact with the virtual objects simply by pointing or gesturing in the desired direction of navigation. However, the feedback provided upon activation of the virtual object may be more varied. Visual feedback in the form of a text message may be presented to the user, such as, "Good choice" or "Try again". Alternatively, the chosen object may move or rotate as appropriate. An auditory message or an appropriate sound effect may also be played. For example, if the user chooses to go through a turnstile the wrong way, the sound of someone grunting may be played.

In addition, realistic background sounds may further augment the environment, to modulate the level of cognitive distractions. For example, at a busy intersection scene where the user needs to decide when it is safe to cross the street (red light versus green light), one may selectively add sounds of vehicular traffic, birds chirping, and a dog barking to raise or lower the level of distractions.

Computer Gaming Control

The present invention may be operable to provide numerous computer games for entertainment purposes, or may be integrated with numerous gaming platforms and games. For example, the present invention may be adapted to any computer game that consists of controlling objects. Some well known examples may be the game Tetris™ or the game Solitaire™. It should be understood, however, that the present invention may be adapted to provide or enhance certain controls associated with any game. From this perspective one of the benefits of the invention is to provide an easy and inexpensive way to tie physical movement to the operation of computer games, with obvious health benefits.

In the Solitaire™ implementation the present invention may provide a means to select a card and move the card to a different location on the game board area. In one embodiment, the virtual space may be occupied by a set of cards displayed in the standard Solitaire™ layout. Each card may be a virtual object. A user may select a card by holding her hand over the area of the image corresponding to the card for a set duration. Once selected, the user may move the card to a second location on the game board area and release it by holding her hand over the area of the image corresponding to the second location. Alternatively, use of both hands may be used, where one hand may select the virtual object corresponding to the card, and the second hand may select a control area consisting of selections such as "hold", "release", etc.

The present invention may also be operable to provide an input means to role playing computer games or any other game. For example, the present invention may be adapted such that the virtual space may be fully occupied by a grid of virtual objects. In this embodiment, the present invention may be operable to track the movement of the user since, when moving, the user must be activating one or more virtual objects at all times. Thus, the present invention may replace traditional game play means such as a joystick, mouse, or keyboard, since the user may directly control the game using real movements. One illustrative example may be a user swinging a virtual sword in a role playing game.

Touch Screen Interface

The present invention may further be operable to provide a means to implement "touch-screen" type functionality on an ordinary display means without the need for an actual touch screen. The ordinary display means may be that of a computer system, personal digital assistant, mobile phone, or any other device or system incorporating a display means.

In this embodiment, the image capture means may be oriented such that the image boundaries correspond to or encompass the display area of the display means. The present invention may be configured such that there is provided a grid of virtual objects across the display area. In this embodiment a user may motion her finger over the screen, and depress her finger over a portion of the screen that she wishes to select. The present invention may track the continuous movement, and upon the user depressing her finger, may interpret the termination of movement as a touch on the display area.

For increased accuracy, a plurality of systems of the present invention may be provided, and oriented to provide a three dimensional virtual space. A person skilled in the art would realize that a three dimensional virtual space may be implemented by orienting two input capture means orthogonally to each other.

Other

It will be appreciated by those skilled in the art that other variations of the one or more embodiments described herein are possible and may be practised without departing from the scope of the present invention. It should be understood that the present invention is not limited to any particular system implementation and that certain system aspects are described for illustration purposes. It should also be understood that while certain aspects of implementation of the invention as a computer program are described, the present invention also contemplates various enhancements to the computer program to provide for example for greater robustness, efficiency, accuracy or otherwise. The invention is not limited to any particular system or computer program architecture, structure, or other attributes. The invention may also be integrated with numerous third party systems or computer programs as a means to provide for, or enhance, motion detection/characterization as described.

What is claimed is:

1. A method for utilizing a motion detection/characterization utility linked to a computer or loaded on the computer operable to perform detection and/or characterization of motion of a target, said method comprising the steps of:
   a. capturing a series of time lapsed images of the target, wherein the target moves as between at least two of such images;
   b. generating a motion distribution in relation to the target across the series of images, said motion distribution being generated by: defining a region of interest for each of the at least two images that corresponds to the target, or movement of the target; comparing the region for each of the at least two images to establish the difference therebetween; estimating the level of activity associated within the region for each of the at least two images; and based on the level of activity determining whether the level of activity connotes motion within the region, or motion having particular characteristics within the region; and
   c. identifying motion of the target based on analysis of the motion distribution.

2. The method of claim 1 comprising the further steps of optionally generating a color distribution for the target based on the series of images, and further identifying the motion based on analysis of the color distribution.

3. The method of claim 2 comprising the further step of analysing the color distribution to achieve greater specificity to the motion detection and/or characterization.

4. The method of claim 2 wherein the color distribution is generated by:
   a. defining a region of interest from a plurality of images that correspond to the target, so as to define a first image sample, and a second image sample, each of the first image sample and second image sample including one or more images;
   b. calculating the average value of each pixel over the first image sample;
   c. establishing the intensity of each image in the second image sample, subtracting the intensity of each such image from the average pixel value in the first image sample, and creating an image model based on such calculations, the image model defining the color distribution.

5. The method of claim 2 wherein the method is operable to adapt to a change in a background scene of the at least two images.

6. The method of claim 1 wherein the motion distribution is generated based on a probability distribution of differences as between the at least two such images signifying motion in the target.

7. The method of claim 1 comprising the further step of determining an area within the region where motion is occurring.

8. The method of claim 1 comprising the further step of defining a motion sensitivity level.

9. The method of claim 8 wherein the level of activity is analyzed to determine whether it meets or exceeds the motion sensitivity level.

10. The method of claim 9 wherein the motion sensitivity level is adjustable.

11. The method of claim 9 wherein the motion sensitivity level is defined automatically.

12. The method of claim 1 comprising the further step of ignoring certain of the identified motions by:
   a. obtaining the region of interest of each of the at least two images to a first plurality of greyscale representations, or converting the region of interest to the first plurality of greyscale representations;
   b. generating a greyscale baseline by averaging, for each pixel in the region of interest, the pixel value of the first plurality of greyscale representations;
   c. obtaining a second plurality of greyscale representations of the region of interest of subsequent images, or converting the region of interest of subsequent images to the second plurality of greyscale representations;
   d. generating a plurality of averages by averaging, for each pixel in the region of interest, the pixel value of the second plurality of greyscale representations;
   e. generating a plurality of fluctuation values by subtracting, for each pixel in the region of interest, the pixel value of the plurality of averages from the pixel value of the greyscale baseline;

f. generating an upper boundary value and a lower boundary value based on a mean and a standard deviation from a statistical distribution of the plurality of fluctuation values;

g. obtaining a single greyscale representation of the region of interest of a further subsequent image, or converting the region of interest of the further subsequent image to the single greyscale representation;

h. generating an average of the sample values generated by subtracting, for each pixel in the region of interest, the pixel value of the single greyscale representations from the pixel value of the greyscale baseline;

i. ignoring detected motion if the average falls between the lower boundary value and the upper boundary value.

13. The method of claim 12 wherein the first plurality of greyscale representations, the second plurality of greyscale representations, and the sample values are buffered.

14. The method of claim 12 wherein the method is operable to adapt to a change in a background scene of the at least two images.

15. An augmented environment system comprising:
a. a computer;
b. an image capture utility linked to or loaded on the computer;
c. optionally, a display linked to the computer;
d. a motion detection/characterization utility linked to the computer or loaded on the computer, the motion detection/characterization utility being operable to:
   i. capture a series of time lapsed images of the target, wherein the target moves between at least two of such images;
   ii. generate a motion distribution in relation to the target across the series of images, said motion distribution being generated by: defining a region of interest for each of the at least two images that corresponds to the target, or movement of the target: comparing the region for each of the at least two images to establish the difference therebetween; estimating the level of activity associated within the region for each of the at least two images; and based on the level of activity determining whether the level of activity connotes motion within the region, or motion having particular characteristics within the region; and
   iii. identify motion of the target based on analysis of the motion distribution.

16. The system of claim 15 further including an aural output means.

17. The system of claim 15 wherein the system is operable to respond to particular movements of an individual with predetermined sounds.

18. The system of claim 15 wherein the system is operable to function as an input means to the computer or a remote computer linked to the computer.

19. The system of claim 15 wherein the system is operable to function as an input means overlaid on a display.

20. A non-transitory computer readable medium comprising computer instructions which when made available to a computer are operable to define in relation to the computer a motion detection/characterization utility that is operable to:
a. capture a series of time lapsed images of the target, wherein the target moves between at least two of such images;
b. generate a motion distribution in relation to the target across the series of images, said motion distribution being generated by: defining a region of interest for each of the at least two images that corresponds to the target, or movement of the target: comparing the region for each of the at least two images to establish the difference therebetween; estimating the level of activity associated within the region for each of the at least two images; and based on the level of activity determining whether the level of activity connotes motion within the region, or motion having particular characteristics within the region; and
c. identify motion of the target based on analysis of the motion distribution.

21. The non-transitory computer readable medium of claim 20 wherein the motion detection/characterization utility enables a user to interface with a computer program.

22. The non-transitory computer readable medium of claim 21 wherein the computer program is a computer game.

* * * * *